US006656884B2

(12) United States Patent
Klintz et al.

(10) Patent No.: US 6,656,884 B2
(45) Date of Patent: Dec. 2, 2003

(54) 3-(4-CYANOPHENYL) URACILS

(75) Inventors: Ralf Klintz, Gruenstadt (DE); Peter Schäfer, Ottersheim (DE); Gerhard Hamprecht, Weinheim (DE); Elisabeth Heistracher, Ludwigshafen (DE); Christoph-Sweder von dem Bussche-Hünnefeld, Mannheim (DE); Norbert Götz, Worms (DE); Albrecht Harreus, Ludwigshafen (DE); Karl-Otto Westphalen, Speyer (DE); Helmut Walter, Obrigheim (DE); Ulf Misslitz, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/323,931

(22) Filed: Dec. 20, 2002

(65) Prior Publication Data
US 2003/0181335 A1 Sep. 25, 2003

Related U.S. Application Data

(62) Division of application No. 08/875,641, filed as application No. PCT/EP96/00312 on Jan. 26, 1996, now abandoned.

(30) Foreign Application Priority Data
Feb. 9, 1995 (DE) .......................... 195 04 188

(51) Int. Cl.$^7$ ..................... C07D 239/54; A01N 43/54
(52) U.S. Cl. ........................ 504/243; 514/312
(58) Field of Search ................... 504/243; 514/312

(56) References Cited

U.S. PATENT DOCUMENTS

| 4,812,164 | A   | 3/1989  | Wenger et al. ............ 71/92 |
| 4,859,229 | A   | 8/1989  | Wenger et al. ............ 71/92 |
| 5,336,663 | A   | 8/1994  | Wenger et al. ............ 504/243 |
| 6,245,715 | B1 * | 6/2001 | Drewes et al. ............ 504/243 |
| 6,355,799 | B1 * | 3/2002 | Gupta et al. .............. 504/242 |
| 6,495,491 | B1 * | 12/2002 | Andree et al. ............. 504/243 |
| 6,545,161 | B2 * | 4/2003 | Gupta et al. .............. 504/243 |

FOREIGN PATENT DOCUMENTS

CA        2225756        1/1997

* cited by examiner

Primary Examiner—John M. Ford
(74) Attorney, Agent, or Firm—Keil & Weinkauf

(57) ABSTRACT 3-(4-Cyanophenyl)uracils of the formula I (I)

wherein
 A is hydrogen, methyl or amino;
 Y is oxygen or sulfur;
 $R^1$ is hydrogen or halogen;
 $R^2$ is hydrogen, halogen, alkyl, haloalkyl, alkylthio, alkylsulfenyl or alkylsulfonyl;
 $R^3$ is hydrogen, halogen or alkyl;
 $R^4$ is hydrogen, haloalkyl; or unsubstituted or substituted alkyl, cycloalkyl, alkenyl, alkynyl, alkylcarbonyl, alkenylcarbonyl, alkynylcarbonyl or alkylsulfonyl, methods and intermediates for their manufacture, and their use as herbicides or for the desiccation or defoliation of plants.

11 Claims, No Drawings

3-(4-CYANOPHENYL) URACILS

This is a divisional application of application Ser. No. 08/875,641, filed under Section 371 on Jul. 30, 1997 now abandoned, based on International Application PCT/EP 96/00312, filed on Jan. 26, 1996.

The present invention relates to novel 3-(4-cyanophenyl) uracils of the general formula I

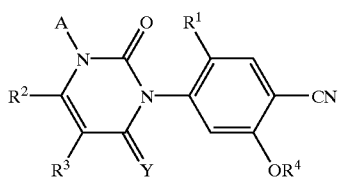

where the variables have the following meanings:

A is hydrogen, methyl or amino;

Y is oxygen or sulfur;

$R^1$ is hydrogen or halogen;

$R^2$ is hydrogen, halogen, $C_1$–$C_6$-alkyl, $C_{1-6}$-haloalkyl, $C_{1-6}$-alkylthio, $C_1$–$C_6$-alkylsulfenyl or $C_1$–$C_6$-alkylsulfonyl;

$R^3$ is hydrogen, halogen or $C_1$–$C_6$-alkyl;

$R^4$ is hydrogen, $C_1$–$C_6$-haloalkyl, $C_1$–$C_6$-alkyl, $C_3$–$C_8$-cyclo-alkyl, $C_3$–$C_6$-alkenyl, $C_3$–$C_6$-alkynyl, ($C_1$–$C_6$-alkyl)-carbonyl, ($C_3$–$C_6$-alkenyl)carbonyl, ($C_3$–$C_6$-alkynyl)carbonyl or alkylsulfonyl, it being possible, if desired, for each of the last-mentioned 8 radicals to have attached to it one to three substituents, in each case selected from the group consisting of halogen, nitro, cyano, hydroxyl, $C_3$–$C_8$-cycloalkyl, $C_1$–$C_6$-alkoxy, $C_3$–$C_8$-Cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfenyl, $C_1$–$C_6$-alkylsulfonyl, $C_1$–$C_6$-alkylideneaminoxy, the phenyl, phenoxy or phenylsulfonyl group which can be unsubstituted or have attached to it one to three substituents, in each case selected from the group consisting of halogen, nitro, cyano, $C_1$–$C_6$-alkyl, $C_1$–$C_6$-alkoxy and $C_1$–$C_6$-haloalkyl, a 3- to 7-membered heterocyclyl or heterocyclyloxy group having one to three hetero atoms selected from the group consisting of two oxygen atoms, two sulfur atoms and 3 nitrogen atoms, it being possible for the heterocycle to be saturated, partially or fully unsaturated or aromatic and, if desired, to have attached to it one to three substituents, in each case selected from the group consisting of halogen, nitro, cyano, $C_1$–$C_6$-alkyl, $C_1$–$C_6$-alkoxy, $C_1$–$C_6$-haloalkyl and ($C_1$–$C_6$-alkyl)carbonyl, a group —CO—$XR^5$, —OCO—$XR^5$ or —N($R^5$)$R^6$ where X is a chemical bond, oxygen, sulfur or —N($R^6$)—;

$R^5$ is hydrogen, $C_1$–$C_6$-alkyl, $C_3$–$C_8$-cycloalkyl, $C_3$–$C_6$-alkenyl, $C_3$–C6-alkynyl, $C_1$–$C_6$-alkoxy-$C_1$–$C_6$-alkyl, ($C_1$–$C_6$-alkoxy)-carbonyl-$C_1$–$C_6$-alkyl, phenyl or phenyl-$C_1$–$C_6$-alkyl, it being possible for the phenyl group and the phenyl ring of the phenylalkyl group to be unsubstituted or to have attached to it one to three radicals, in each case selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkyl)carbonyl or X and $R^5$ together form a 3- to 7-membered heterocycle, bonded via nitrogen and having one to three hetero atoms selected from the group consisting of two oxygen atoms, two sulfur atoms and 3 nitrogen atoms, it being possible for the heterocycle to be saturated, partially or fully unsaturated or aromatic and, if desired, to have attached to it one to three substituents, in each case selected from the group consisting of halogen, nitro, cyano, $C_1$–$C_6$-alkyl, $C_1$–$C_6$-haloalkyl $C_1$–$C_6$-alkoxy and ($C_1$–$C_6$-alkyl)carbonyl; and $R^6$ represents hydrogen, hydroxyl, $C_1$–$C_6$-alkyl, $C_3$–$C_8$-cycloalkyl or $C_1$–$C_6$-alkoxy, and the agriculturally useful salts of those compounds I where A is hydrogen.

The invention furthermore relates to the use of the compounds I as herbicides and/or for the desiccation and/or defoliation of plants, herbicidal compositions and compositions for desiccating and/or defoliating plants which comprise the compounds I as active ingredients, methods of controlling undesirable vegetation and for desiccating and/or defoliating plants using the compounds I, processes for the preparation of the compounds I and of herbicidal compositions and compositions for desiccating and/or defoliating plants using the compounds I, and novel intermediates of the formulae III and IV from which the compounds I are obtainable.

Regarding the compounds I where A=hydrogen or methyl, EP-A 255 047 is of particular importance since it discloses quite generally 3-aryluracils of the formula II

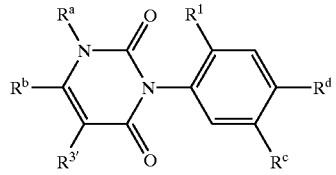

where $R^a$ is hydrogen, $C_{1-4}$-alkyl, $C_{1-4}$-haloalkyl, formyl or $C_{2-6}$-alkanoyl, $R^b$ is $C_{1-4}$-alkyl or $C_{1-4}$-haloalkyl, $R^{3'}$ is hydrogen, halogen or $C_1$–$C_4$-alkyl, $R^c$ is an ether group or a radical R—CO—O—, R—CS—O— or R—SO$_2$—O— and $R^d$ is halogen or cyano and the salts of the compounds II where $R^a$=hydrogen, as herbicides.

Examples of 3-phenyluracils in which the phenyl ring carries a cyano group para to the uracil radical ($R^d$), and their herbicidal action, however, are not revealed by this document.

Certain 1-amino-3-phenyluracils which, however, do not carry a cyano group on the phenyl ring have already been disclosed as herbicides in EP-A-517 181 and JP-A 05/025 143.

However, the herbicidal or desiccant/defoliant properties of the known compounds are not always entirely satisfactory.

It was therefore an object of the present invention to provide novel, in particular herbicidally active compounds, which allow better, tailored control of undesirable plants than this was possible to date.

The object also extends to the provision of novel compounds which act as desiccants/defoliants.

We have found that this object is achieved by the 3-(4-cyanophenyl)uracils of the formula I and their herbicidal action.

There have furthermore been found herbicidal compositions which comprise the compounds I and have a very good herbicidal action. There have also been found processes for preparing these compositions and methods of controlling undesirable vegetation using the compounds I.

It has furthermore been found that the compounds I are also suitable for defoliating and desiccating parts of plants, suitable plants being crop plants such as cotton, potatoes, oilseed rape, sunflowers, soybeans or field beans, in particular cotton. Thus, there have been found compositions for the desiccation and/or defoliation of plants, processes for the preparation of these compositions, and methods of desiccating and/or defoliating plants using the compounds I.

Depending on the substitution pattern, the compounds of the formula I can have one or more chiral centers, in which case they are present as enantiomer or diastereomer mixtures. The invention relates to the pure enantiomers or diastereomers and to their mixtures.

If A is hydrogen, the 3-(4-cyanophenyl)uracils I can be present in the form of their agriculturally useful salts, the type of salt not being critical, as a rule. In general, suitable salts are salts of those bases which do not adversely affect the herbicidal action in comparison with the free compounds I.

Particularly suitable basic salts are those of the alkali metals, preferably sodium and potassium salts, of the alkaline earth metals, preferably calcium and magnesium salts, those of the transition metals, preferably zinc and iron salts, and also ammonium salts where, if desired, the ammonium ion can have attached to it one to three $C_1$–$C_4$-alkyl or hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl(2-hydroxyethyl)ammonium salts, furthermore phosphonium salts, sulfonium salts, such as, preferably, tri($C_1$–$C_4$-alkyl)sulfonium salts, and sulfoxonium salts, such as, preferably, tri($C_1$–$C_4$-alkyl)sulfoxonium salts.

The organic moieties mentioned for the substituents $R^1$ to $R^6$ or as radicals on phenyl rings or heterocycles are—like the meaning halogen—collective terms for individual enumerations of the individual group members. All carbon chains, ie. all alkyl, haloalkyl, alkoxy, alkylthio, alkylsulfenyl, alkylsulfonyl, alkylcarbonyl, alkenyl, alkenyloxy, alkenylcarbonyl, alkynyl, alkynyloxy, alkynylcarbonyl and alkylideneaminoxy moieties can be straight-chain or branched. Unless otherwise indicated, halogenated substituents preferably have attached to them one to five identical or different halogen atoms.

Examples of individual meanings are:

halogen: fluorine, chlorine, bromine or iodine;

$C_1$–$C_4$-alkyl and the alkyl moieties of $C_1$–$C_6$-alkoxy-$C_1$–$C_6$-alkyl and ($C_1$–$C_6$-alkoxy)carbonyl-$C_1$–$C_6$-alkyl: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, 1,1-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl;

$C_1$–$C_6$-haloalkyl: a $C_1$–$C_6$-alkyl radical as mentioned above which is partially or fully substituted by fluorine, chlorine, bromine and/or iodine, eg. chloromethyl, dichloro-methyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromo-ethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

phenyl-$C_1$–$C_6$-alkyl: eg. benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 3-phenylbut-2-yl, 4-phenylbut-2-yl, 1-(phenylmethyl)eth-1-yl, 1-(phenylmethyl)-1-(methyl)eth-1-yl and 1-(phenylmethyl)prop-1-yl, preferably benzyl, 2-phenylethyl and 2-phenylhex-6-yl;

$C_3$–$C_6$-alkenyl and the alkenyl moieties of $C_3$–$C_6$-alkenyloxy and ($C_3$–$C_6$-alkenyl)carbonyl: prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methyl-prop-2-en-1-yl or 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethyl-but-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethyl-prop-2-en-1-yl, 1-ethyl-1-methylprop-2-en-1-yl, 1-ethyl-2-methylprop-1-en-1-yl or 1-ethyl-2-methylprop-2-en-1-yl;

$C_3$–$C_6$-alkynyl and the alkynyl moieties of $C_3$–$C_6$-alkynyloxy and ($C_3$–$C_6$-alkynyl)carbonyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methyl-pent-2-yn-5-yl;

$C_1$–$C_6$-alkoxy and the alkoxy moieties of $C_1$–$C_6$-alkoxy-$C_1$–$C_6$-alkyl and ($C_1$–$C_6$-alkoxy)carbonyl-$C_1$–$C_6$-alkyl: methoxy, ethoxy, n-propoxy, 1-methylethoxy, n-butoxy, 1-methylpropoxy, 2-methylpropoxy or 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_6$-alkylthio: methylthio, ethylthio, n-propylthio, 1-methylethylthio, n-butylthio, 1-methylpropylthio, 2-methylpropylthio, 1,1-dimethylethylthio, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutyl-thio, 2-ethylbutylthio, 1,1,2-trimethylpropylthio, 1,2,2-trimethylpropylthio, 1-ethyl-1-methylpropylthio or 1-ethyl-2-methylpropylthio; ($C_1$–$C_6$-alkyl)carbonyl: methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_1$–$C_4$-alkylsulfenyl: methylsulfenyl, ethylsulfenyl, n-propylsulfenyl, 1-methylethylsulfenyl, n-butylsulfenyl, 1-methylpropylsulfenyl, 2-methylpropylsulfenyl, 1,1-dimethylethylsulfenyl, n-pentylsulfenyl, 1-methylbutylsulfenyl, 2-methylbutylsulfenyl, 3-methylbutylsulfenyl, 2,2-dimethylpropylsulfenyl, 1-ethylpropylsulfenyl, 1,1-dimethylpropylsulfenyl, 1,2-dimethylpropylsulfenyl, n-hexylsulfenyl, 1-methylpentylsulfenyl, 2-methylpentylsulfenyl, 3-methylpentylsulfenyl, 4-methylpentylsulfenyl, 1,1-dimethylbutylsulfenyl, 1,2-dimethylbutylsulfenyl, 1,3-dimethylbutylsulfenyl, 2,2-dimethylbutylsulfenyl, 2,3-dimethylbutylsulfenyl, 3,3-dimethylbutylsulfenyl, 1-ethylbutylsulfenyl, 2-ethylbutylsulfenyl, 1,1,2-trimethylpropylsulfenyl, 1,2,2-trimethylpropylsulfenyl, 1-ethyl-1-methylpropylsulfenyl or 1-ethyl-2-methylpropylsulfenyl;

$C_1$–$C_4$-alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_6$-alkylideneaminoxy: acetylideneaminoxy, 1-propylideneaminoxy, 2-propylideneaminoxy, 1-butylideneaminoxy, 2-butylideneaminoxy or 2-hexylideneaminoxy;

$C_3$–$C_8$-cycloalkyl: cyclopropyl, cyclobutyl, cyclopentyl, cyclohexyl, cycloheptyl and cyclooctyl;

$C_3$–$C_8$-cycloalkoxy: cyclopropyloxy, cyclobutyloxy, cyclopentyloxy, cyclohexyloxy, cycloheptyloxy and cyclooctyloxy.

Examples of 3- to 7-membered heterocycles are oxiranyl, aziridinyl, oxetanyl, tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, dioxolanyl, such as 1,3-dioxolan-2-yl and 1,3-dioxolan-4-yl, 1,3-dioxan-2-yl, 1,3-dioxan-4-yl, 1,3-dithian-2-yl, 1,2,4-oxadiazolidinyl, 1,3,4-oxadiazolidinyl, 1,2,4-thiadiazolidinyl, 1,3,4-thiadiazolidinyl, 1,2,4-triazolidinyl, 1,3,4-triazolidinyl, 2,3-dihydrofuryl, 2,5-dihydrofuryl, 2,3-dihydrothienyl, 2,5-dihydrothienyl, 2,3-pyrrolinyl, 2,5-pyrrolinyl, 2,3-isoxazolinyl, 3,4-isoxazolinyl, 4,5-isoxazolinyl, 2,3-isothiazolinyl, 3,4-isothiazolinyl, 4,5-isothiazolinyl, 2,3-dihydropyrazolyl, 3,4-dihydropyrazolyl, 4,5-dihydropyrazolyl, 2,3-dihydrooxazolyl, 3,4-dihydrooxazolyl, thiazolyl, imidazolyl, 1,2,4-oxadiazolyl, 1,3,4-oxadiazolyl, 1,2,4-thiadiazolyl, 1,3,4-thiadiazolyl, 1,2,4-triazolyl and 1,3,4-triazolyl, piperidinyl, tetrahydropyridazinyl, tetrahydropyrimidinyl, tetrahydropyrazinyl, 1,3,5-tetrahydrotriazinyl and 1,2,4-tetrahydrotriazinyl, and the following heteroaromatics:

2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-1-yl, 1,2,4-triazol-3-yl, 1,2,4-triazol-4-yl, 1,3,4-oxadiazol-2-yl, 1,3,4-thiadiazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl, in particular pyridyl, pyrimidyl, furanyl and thienyl.

All phenyl- and heterocyclic rings are preferably unsubstituted or have attached to them a halogen, methyl, trifluoromethyl or methoxy substituent.

With a view to the use of the novel compounds of the formula I as herbicides and/or as compounds with a defoliant/desiccant action, the variables preferably have the following meanings, in each case on their own or in combination:

A is amino or methyl;

Y is oxygen;

$R^1$ is hydrogen, fluorine or chlorine, in particular hydrogen or fluorine;

$R^2$ is $C_1$–$C_6$-alkyl, $C_1$–$C_6$-haloalkyl or $C_1$–$C_6$-alkylsulfonyl, in particular $C_1$–$C_4$-haloalkyl, particularly preferably trifluoromethyl, chlorodifluoromethyl or pentafluoroethyl;

$R^3$ is hydrogen or halogen, in particular hydrogen, chlorine or bromine;

$R^4$ is hydrogen, $C_1$–$C_6$-haloalkyl, $C_1$–$C_6$-alkyl, $C_{3-8}$-cycloalkyl, $C_3$–$C_6$-alkenyl, $C_3$–$C_6$-alkynyl, ($C_1$–$C_6$-alkyl)-carbonyl, ($C_3$–$C_6$-alkenyl)carbonyl or ($C_3$–$C6$-alkynyl)-carbonyl, it being possible, if desired, for each of the last-mentioned 8 radicals to have attached to it one or two substituents, in each case selected from the group consisting of halogen, nitro, cyano, hydroxyl, $C_3$–$C_8$-cycloalkyl, $C_1$–$C_6$-alkoxy, $C_3$–$C_8$-cycloalkoxy, $C_3$–$C_6$-alkenyloxy, $C_3$–$C_6$-alkynyloxy, $C_1$–$C_6$-alkoxy-$C_1$–$C_6$-alkoxy, $C_1$–$C_6$-alkylthio, $C_1$–$C_6$-alkylsulfenyl, $C_1$–$C_6$-alkylsulfonyl, $C_1$–$C_6$-alkylideneaminoxy, —O—$XR^5$, —OCO—$XR^5$ or —N($R^5$)$R^6$, in particular hydrogen, $C_1$–$C_4$-alkyl, $C_3$–$C_6$-cycloalkyl, $C_3$–$C_4$-alkenyl, $C_3$–$C_4$-alkynyl, $C_1$–$C_4$-haloalkyl, $C_1$–$C_4$-alkoxy-$C_1$–$C_4$-alkyl, ($C_1$–$C_4$-alkyl)carbonyl, —$CH_2$—CO—$XR^5$, —CH($CH_3$)—CO—$XR^5$ or $C_1$–$C_4$-cyanoalkyl, such as cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl and 2-cyano-methylprop-2-yl;

X is a chemical bond, oxygen or —N(R6)—;

$R^5$ is hydrogen, $C_1$–$C_6$-alkyl, $C_3$–$C_8$-cycloalkyl, $C_3$–$C_6$-alkenyl, $C_3$–$C_6$-alkynyl, $C_1$–$C_6$-alkoxy-$C_1$–$C_6$-alkyl or ($C_1$–$C_6$-alkoxy)carbonyl-$C_1$–$C_6$-alkyl, in particular hydrogen, $C_1$–$C_6$-alkyl, $C_3$–$C_8$-cycloalkyl, $C_1$–$C_6$-alkoxy-$C_1$–$C_6$-alkyl or ($C_1$–$C_6$-alkoxy)carbonyl-$C_1$–$C_6$-alkyl, $R^6$ is hydrogen, $C_1$–$C_6$-alkyl or $C_1$–$C_6$-alkoxy.

Very particularly preferred are the compounds Ia which are listed in Table 1 below (=I where A=amino, Y=oxygen, $R^1$=fluorine, $R^2$=trifluoromethyl, $R^3$=hydrogen):

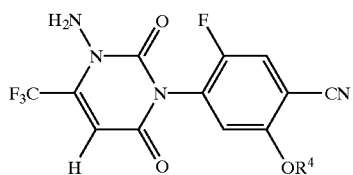

Ia

TABLE 1

| No. | $R^4$ |
|---|---|
| Ia.01 | H |
| Ia.02 | $CH_3$ |
| Ia.03 | $C_2H_5$ |
| Ia.04 | n-$C_3H_7$ |
| Ia.05 | $CH(CH_3)_2$ |
| Ia.06 | n-$C_4H_9$ |
| Ia.07 | i-$C_4H_9$ |
| Ia.08 | s-$C_4H_9$ |
| Ia.09 | $C(CH_3)_3$ |
| Ia.10 | cyclopropyl |
| Ia.11 | cyclobutyl |
| Ia.12 | cyclopentyl |
| Ia.13 | cyclohexyl |
| Ia.14 | cycloheptyl |
| Ia.15 | cyclooctyl |
| Ia.16 | $CH_2CN$ |
| Ia.17 | $CH_2CH_2CN$ |
| Ia.18 | $CH(CH_3)CN$ |
| Ia.19 | $C(CH_3)_2CN$ |
| Ia.20 | $C(CH_3)_2CH_2CN$ |
| Ia.21 | $CH_2Cl$ |
| Ia.22 | $CH_2CH_2Cl$ |
| Ia.23 | $CH(CH_3)CH_2Cl$ |
| Ia.24 | $CH_2CF_3$ |
| Ia.25 | $CHCl_2$ |
| Ia.26 | $CF_2Cl$ |
| Ia.27 | $CF_3$ |
| Ia.28 | $C_2F_5$ |
| Ia.29 | $CF_2H$ |
| Ia.30 | $CH_2$—CH=$CH_2$ |
| Ia.31 | $CH(CH_3)$—CH=$CH_2$ |
| Ia.32 | $CH_2$—CH=CH—$CH_3$ |
| Ia.33 | $CH_2$—C≡CH |
| Ia.34 | $CH(CH_3)$—C≡CH |
| Ia.35 | $C(CH_3)_2$—C≡CH |
| Ia.36 | $CH_2$—COOH |
| Ia.37 | $CH_2$—CO—$OCH_3$ |
| Ia.38 | $CH_2$—CO—$OC_2H_5$ |
| Ia.39 | $CH_2$—CO—O-n-$C_3H_7$ |
| Ia.40 | $CH_2$—CO—$OCH(CH_3)_2$ |
| Ia.41 | $CH(CH_3)$—CO—$OCH_3$ |
| Ia.42 | $CH(CH_3)$—CO—$OC_2H_5$ |
| Ia.43 | $CH(CH_3)$—CO—O-n-$C_3H_7$ |
| Ia.44 | $CH(CH_3)$—CO—$OC(CH_3)_2$ |
| Ia.45 | $CH_2$—COO—$(CH_2)_2$—$OCH_3$ |
| Ia.46 | $CH_2$—COO—$(CH_2)_2$—$OCH_3$ |
| Ia.47 | $CH(CH_3)$—COO—$(CH_2)_2$—$OCH_3$ |
| Ia.48 | $CH(CH_3)$—COO—$(CH_2)_2$—$OC_2H_5$ |
| Ia.49 | $CH_2$—$CONH_2$ |
| Ia.50 | $CH_2$—$CONHCH_3$ |
| Ia.51 | $CH_2$—$CONHC_2H_5$ |
| Ia.52 | $CH_2$—$CON(CH_3)_2$ |
| Ia.53 | $CH(CH_3)$—$CONH_2$ |
| Ia.54 | $CH(CH_3)$—$CONHCH_3$ |
| Ia.55 | $CH(CH_3)$—$CONHC_2H_5$ |
| Ia.56 | $CH(CH_3)$—$CON(CH_3)_2$ |
| Ia.57 | CO—$CH_3$ |
| Ia.58 | CO—$C_2H_5$ |
| Ia.59 | CO—$CH(CH_3)_2$ |
| Ia.60 | CO-n-$C_4H_9$ |
| Ia.61 | CO-cyclopropyl |
| Ia.62 | CO-cyclopentyl |
| Ia.63 | CO—$CF_3$ |
| Ia.64 | CO—$OCH_3$ |

TABLE 1-continued

| No. | R⁴ |
|---|---|
| Ia.65 | CO—OC$_2$H$_5$ |
| Ia.66 | SO$_2$—CH$_3$ |
| Ia.67 | CH$_2$—SCH$_3$ |
| Ia.68 | (CH$_2$)$_2$—SCH$_3$ |
| Ia.69 | (CH$_2$)$_2$—SC$_2$H$_5$ |
| Ia.70 | (CH$_2$)$_2$—SO—CH$_3$ |
| Ia.71 | (CH$_2$)$_2$—SO$_2$—CH$_3$ |
| Ia.72 | (CH$_2$)$_2$—SO—CH$_3$ |
| Ia.73 | (CH$_2$)$_2$-cyclopropyl |
| Ia.74 | (CH$_2$)$_2$-cyclopentyl |
| Ia.75 | (CH$_2$)$_2$—ON═C(CH$_3$)$_2$ |
| Ia.76 | (CH$_2$)$_3$—ON═C(CH$_3$)$_2$ |
| Ia.77 | (CH$_2$)$_2$—NO$_2$ |
| Ia.78 | (CH$_2$)$_2$—NH$_2$ |
| Ia.79 | (CH$_2$)$_2$—NHCH$_3$ |
| Ia.80 | (CH$_2$)$_2$—NH(CH$_3$)$_2$ |
| Ia.81 | CH$_2$—OCH$_3$ |
| Ia.82 | CH(CH$_3$)—OCH$_3$ |
| Ia.83 | CH(CH$_3$)—OC$_2$H$_5$ |
| Ia.84 | CH(CH$_3$)CH$_2$—OCH$_3$ |
| Ia.85 | (CH$_2$)$_2$OH |
| Ia.86 | CH$_2$—OC$_2$H$_5$ |
| Ia.87 | CH$_2$COO-(4-acetoxytetrahydrofuran-3-yl) |
| Ia.88 | CH$_2$OCOCH$_3$ |
| Ia.89 | CH$_2$OCOC$_2$H$_5$ |
| Ia.90 | CH$_2$C$_6$H$_5$ |
| Ia.91 | (CH$_2$)$_2$—C$_6$H$_5$ |
| Ia.92 | CH$_2$—(4-Cl—C$_6$H$_4$) |
| Ia.93 | CH$_2$—(4-CF$_3$—C$_6$H$_4$) |
| Ia.94 | CH$_2$—(3-NO$_2$—C$_6$H$_4$) |

Other particularly preferred 3-(4-cyanophenyl)uracils of the formula I are those which follow:

the compounds Ib.01–Ib.94, which only differ from the corresponding compounds Ia.01–Ia.94 by the fact that R$^1$ is hydrogen:

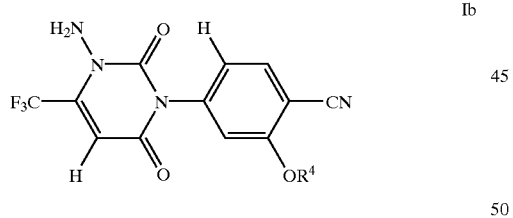

Ib the compounds Ic.01–Ic.94, which only differ from the corresponding compounds Ia.01–Ia.94 by the fact that R$^1$ is chlorine:

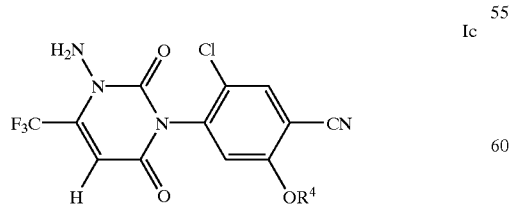

Ic the compounds Id.01–Id.94, which only differ from the corresponding compounds Ia.01–Ia.94 by the fact that A is methyl:

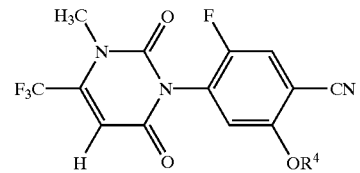

Id the compounds Ie.01–Ie.94, which only differ from the corresponding compounds Ia.01–Ia.94 by the fact that A is hydrogen:

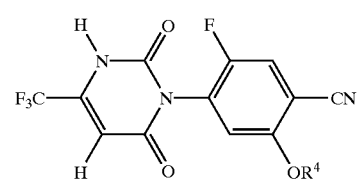

Ie the compounds If.01–If.94, which only differ from the corresponding compounds Ia.01–Ia.94 by the fact that R$^1$ is hydrogen and A is methyl:

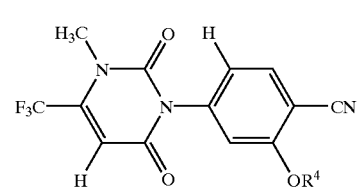

If the compounds Ig.01–Ig.94, which only differ from the corresponding compounds Ia.01–Ia.94 by the fact that R$^1$ and A are hydrogen:

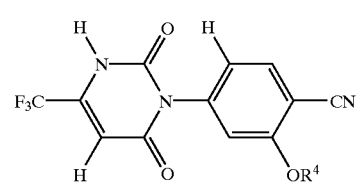

Ig the compounds Ih.01–Ih.94, which only differ from the corresponding compounds Ia.01–Ia.94 by the fact that R$^1$ is chlorine and A is methyl:

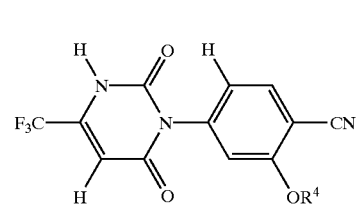

Ih the compounds Ii.01–Ii.94, which only differ from the corresponding compounds Ia.01–Ia.94 by the fact that R$^1$ is chlorine and A is hydrogen:

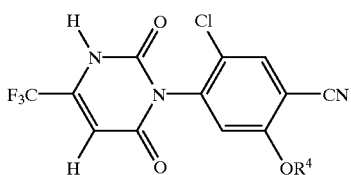

Ii the compounds Ik.01–Ik.94, which only differ from the corresponding compounds Ia.01–Ia.94 by the fact that $R^3$ is chlorine:

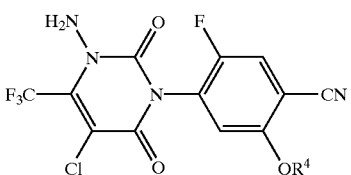

Ik the compounds Il.01–Il.94, which only differ from the corresponding compounds Ia.01–Ia.94 by the fact that $R^3$ is chlorine and A is methyl:

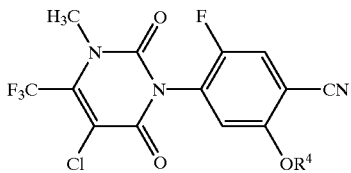

Il the compounds Im.01–Im.94, which only differ from the corresponding compounds Ia.01–Ia.94 by the fact that $R^3$ is chlorine and A is hydrogen:

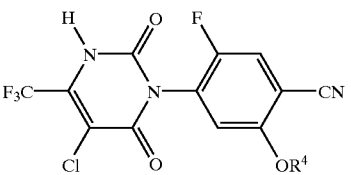

Im the compounds In.01–In.94, which only differ from the corresponding compounds Ia.01–Ia.94 by the fact that $R^1$ and $R^3$ are chlorine:

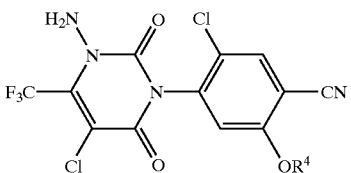

In the compounds Io.01–Io.94, which only differ from the corresponding compounds Ia.01–Ia.94 by the fact that A is methyl, $R^1$ is hydrogen and $R^3$ is chlorine:

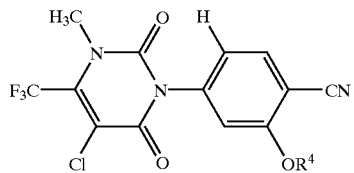

Io the compounds Ip.01–Ip.94, which only differ from the corresponding compounds Ia.01–Ia.94 by the fact that A is methyl and $R^1$ and $R^3$ are chlorine:

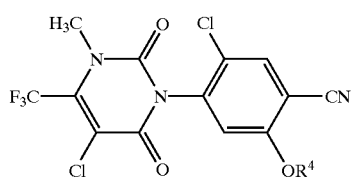

Ip

The 3-(4-cyanophenyl)uracils of the formula I can be obtained by various routes, for example by one of the following processes:

Process A):

Cyclization of an enamine ester of the formula III or of an enamine carboxylate of the formula IV in the presence of a base:

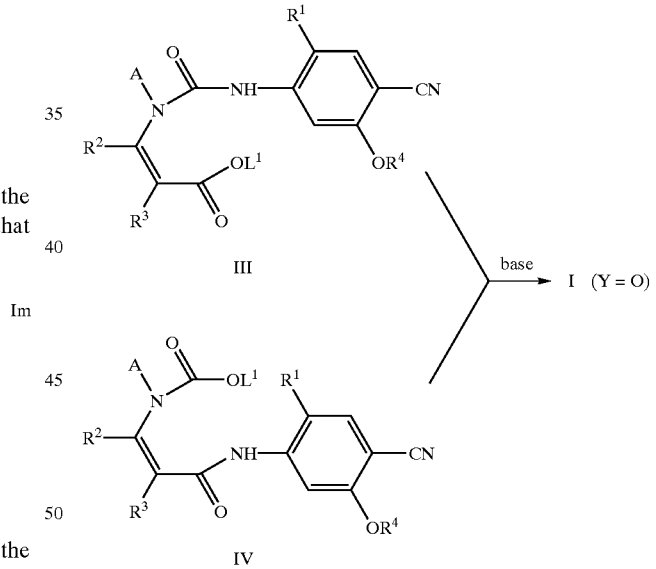

$L^1$ is low-molecular-weight alkyl, preferably $C_1$–$C_4$-alkyl, or phenyl.

As a rule, the cyclization is carried out in an inert organic solvent or diluent which is aprotic, for example in an aliphatic or cyclic ether, such as 1,2-dimethoxyethane, tetrahydrofuran and dioxane, in an aromatic, such as benzene and toluene, or in a polar solvent, such as dimethylformamide and dimethyl sulfoxide. Mixtures of polar solvents and a hydrocarbon, such as n-hexane, are also suitable. Depending on the starting material, water may also be suitable as the diluent.

Suitable bases are, preferably, alkali metal alcoholates, in particular the sodium alcoholates, alkali metal hydroxides, in particular sodium hydroxide and potassium hydroxide, alkali metal carbonates, in particular sodium carbonate and potassium carbonate, and metal hydrides, in particular sodium hydride. If sodium hydride is used as the base, it has proved advantageous to carry out the process in an aliphatic or cyclic ether, in dimethylformamide or in dimethyl sulfoxide.

0.5 times to twice the molar amount of base based on the amount of III or IV is generally sufficient to carry out the reaction successfully.

In general, the reaction temperature is from (−78)° C. to the boiling point of the reaction mixture in question, in particular from (−60) to 60° C.

If A in formula III or IV is hydrogen, the process product is obtained as a metal salt, the metal corresponding to the cation of the base used. The salt can be isolated and purified in a manner known per se or, if desired, converted using an acid to obtain the free compound I where A=hydrogen.

Process B):

Methylation of a compound I where A is hydrogen in the presence of a base:

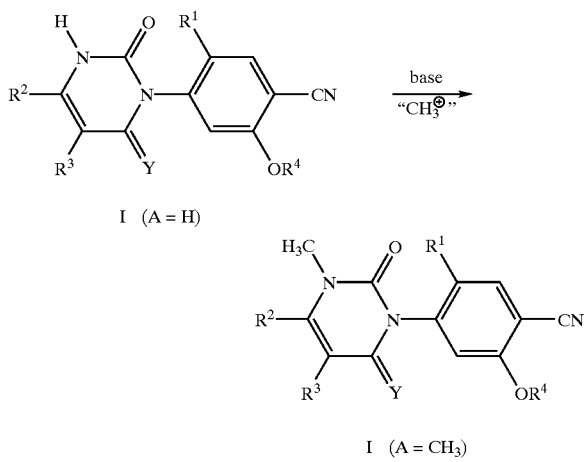

Examples of suitable methylating agents are methyl halides, preferably methyl chloride, methyl iodide or methyl bromide, and also dimethyl sulfate, methyl methanesulfonate (methyl mesylate), methyl benzenesulfonate, methyl p-toluenesulfonate (methyl tosylate), methyl p-bromobenzenesulfonate (methyl brosylate), methyl trifluoromethanesulfonate (methyl triflate) and diazomethane.

As a rule, the process is carried out in an inert organic solvent or in an aprotic solvent, eg. in an aliphatic or cyclic ether, preferably in 1,2-dimethoxyethane, tetrahydrofuran or dioxane, in an aliphatic ketone, preferably in acetone, in an amide, preferably in dimethylformamide, in a sulfoxide, preferably in dimethyl sulfoxide, in a urea, such as tetramethylurea and 1,3-dimethyltetrahydro-2(1H)-pyrimidinone, in a carboxylic ester, such as ethyl acetate, or in a halogenated aliphatic or aromatic hydrocarbon, such as dichloromethane and chlorobenzene.

Suitable bases are inorganic bases, eg. carbonates, such as sodium carbonate and potassium carbonate, hydrogen carbonates, such as sodium hydrogen carbonate or potassium hydrogen carbonate, or alkali metal hydrides, such as sodium hydride and potassium hydride, and also organic bases, eg. amines, such as triethylamine, pyridine and N,N-diethylaniline, or alkali metal alcoholates, such as sodium methanolate, sodium ethanolate and potassium tert-butanolate.

The amount of base and methylating agent is preferably 0.5 times to twice the molar amount based on the amount of starting compound.

In general, the reaction temperature is from 0° C. to the boiling point of the reaction mixture, in particular from 0 to 60° C. A preferred process variant consists in methylating the salt of I, which has been obtained by cyclizing III (A=H) or IV (A=H) in accordance with process A) without isolating it from the reaction mixture, which can still contain excess base, eg. sodium hydride, sodium alcoholate or sodium carbonate.

If the salts of those compounds I where A is hydrogen cannot be prepared directly by the cyclization under alkaline conditions, which has been described as method a), they can also be obtained from the process products obtained by method a) in a manner known per se. For this purpose, for example, the aqueous solution of an inorganic or organic base is treated with the substituted 3-(4-cyanophenyl)uracil I where A is hydrogen. Salt formation usually takes place at sufficiently high rates at as little as 20–25° C.

It is particularly advantageous to prepare the sodium salt by dissolving the 3-(4-cyanophenyl)uracil I (A=hydrogen) in aqueous sodium hydroxide solution at 20–25° C., using approximately equivalent amounts of 3-(4-cyanophenyl) uracil and sodium hydroxide. The salt of the 3-(4-cyanophenyl)uracil can then be isolated for example by precipitation with a suitable inert solvent or by evaporating the solvent.

Salts of the 3-(4-cyanophenyl)uracils whose metal ion is not an alkali metal ion can generally be prepared by double decomposition of the corresponding alkali metal salt in aqueous solution. 3-(4-cyanophenyl)uracil metal salts which are insoluble in water can be prepared in this manner, for example.

Process C):

Reaction of a 3-(4-cyanophenyl)uracil of the formula I where A is hydrogen with an electrophilic aminating reagent in the presence of a base:

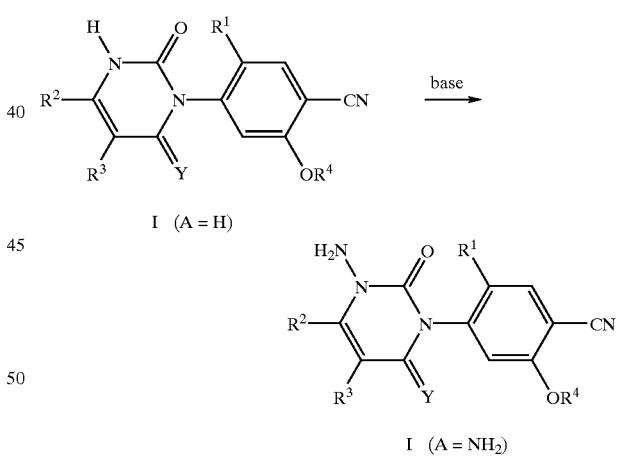

An aminating reagent which has proved useful to date is 2,4-dinitrophenoxyamine, but hydroxylamine-O-sulfonic acid (HOSA), which has been disclosed in the literature as aminating reagent, can, for example, also be used (cf., for example, E. Hofer et al., Synthesis 1983, 466; W. Friedrichsen et al., Heterocycles 20 (1983) 1271; H. Hart et al., Tetrahedron Lett. 25 (1984) 2073; B. Vercek et al., Monatsh. Chem. 114 (1983) 789; G. Sosnousky et al., Z. Naturforsch. 38 (1983) 884; R. S. Atkinson et al., J. Chem. Soc. Perkin Trans. 1987, 2787).

Amination can be carried out in a manner known per se (see, for example, T. Sheradsky, Tetrahedron Lett. 1948, 1909; M. P. Wentland et al., J. Med. Chem. 27 (1984) 1103, and, in particular, EP-A 240 194, EP-A 476 697 and EP-A 517 181, which teach the amination of uracils).

The reaction is usually carried out in a polar solvent, eg. in dimethylformamide, N-methylpyrrolidone, dimethyl sulfoxide or in ethyl acetate, which has proved particularly useful to date.

Examples of suitable bases are alkali metal carbonates, such as potassium carbonate, alkali metal alcoholates, such as sodium methylate and potassium tert-butanolate, or alkali metal hydrides, such as sodium hydride.

The amount of base and aminating agent is preferably in each case 0.5 times to twice the molar amount based on the amount of starting compound.

Depending on the meaning of $R^4$, it may be necessary to protect this substituent in a manner known per se prior to amination. This is particularly to be recommended if $R^4$ is hydrogen.

Process D):

Sulfuration of a 3-(4-cyanophenyl)uracil of the formula I where Y=oxygen:

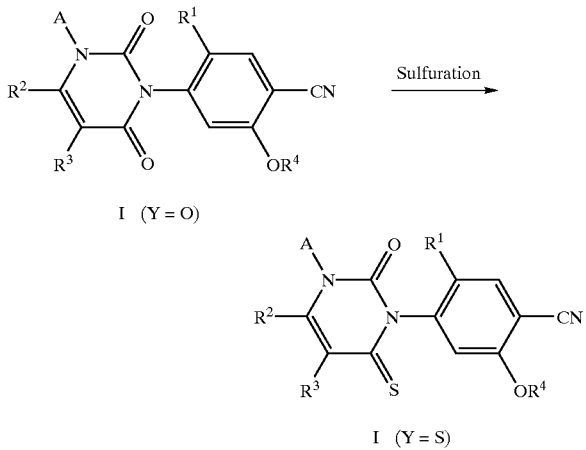

I (Y = O)

I (Y = S)

The sulfuration is generally carried out in an inert solvent or diluent, for example in an aromatic hydrocarbon, such as toluene and the xylenes, in an ether, such as diethyl ether, 1,2-dimethoxyethane and tetrahydrofuran, or in an organic amine, such as pyridine.

Particularly suitable sulfurating reagents are phosphorus (V) sulfide and 2,4-bis(4-methoxyphenyl)-1,3,2,4-dithiadiphosphetane-2,4-dithione ("Lawesson's reagent").

1 to 5 times the molar amount based on the starting compound to be sulfurized is generally sufficient for an essentially complete reaction.

The reaction temperature usually is from 20 to 200° C., preferably 40° C. to the boiling point of the reaction mixture.

Process E):

Ether cleavage of a 3-(4-cyanophenyl)uracil of the formula I where $R^4$ is an unsubstituted or substituted alkyl, cycloalkyl, alkenyl, alkynyl or benzyl:

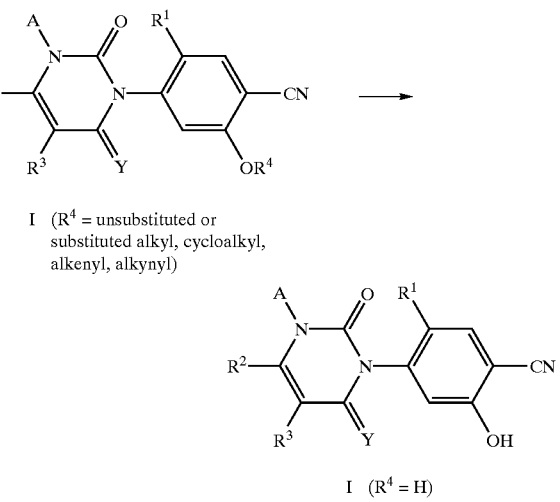

I ($R^4$ = unsubstituted or substituted alkyl, cycloalkyl, alkenyl, alkynyl)

I ($R^4$ = H)

The ether cleavage is usually effected by means of an acid, eg. by means of hydrogen bromide, hydrogen iodide or pyridinium hydrochloride, by means of a Lewis acid, such as aluminum trichloride, aluminum tribromide, aluminum triiodide, boron trichloride, boron tribromide, boron trifluoride and iron trichloride, or by means of trimethylsilyl iodide. Other useful substances for cleaving the ether bond are, however, also lithium salts, such as lithium chloride, or mixtures of an inorganic iodide and trimethylsilyl chloride. In individual cases, for example when $R^4$ is benzyl, the bond can also be cleaved under hydrogenation conditions using hydrogen in the presence of a hydrogenation catalyst, such as platinum and palladium on active charcoal.

Allyl ethers ($R^4$=allyl) can furthermore be converted into the corresponding phenols in a manner known per se for this purpose, for example by isomerization in the presence of a transition metal catalyst to give the enol ether and cleavage of the latter, preferably under mildly acidic conditions (cf., for example, T. Greene and P. G. M. Wutz in "Protective Groups in Organic Synthesis", John Wiley & Sons, 2nd Edition, New York 1991, p. 42 et seq.).

The process is generally carried out in an inert solvent or diluent, eg. in an aliphatic, cyclic or aromatic hydrocarbon, such as n-pentane, petroleum ether, cyclohexane, benzene, toluene or xylene, an aliphatic or cyclic ether, such as diethyl ether, tert-butyl methyl ether, dimethoxyethane and tetrahydrofuran, an aliphatic or aromatic halogenated hydrocarbon, such as dichloromethane, chloroform, chlorobenzene, 1,2-dichloroethane and the dichlorobenzenes, an alcohol, such as methanol, ethanol and tert-butanol, an amide, such as dimethylformamide and N-methylpyrrolidone, an amine, such as ammonia, or in a mixture of these.

It may also be advantageous to carry out the reaction in the absence of a solvent.

With regard to particularly preferred embodiments, mention may be made of the information given in Houben-Weyl, "Methoden der Organischen Chemie" [Methods in Organic Chemistry], Georg Thieme Verlag, 4th Edition, Stuttgart 1979, Vol. 6/1a/1, p. 309 et seq., and in R. C. Larock, "Comprehensive Organic Transformations", VCH-Publishers, Weinheim 1989, p. 501 et seq., and the literature cited in these publications.

Process F):

Alkylation of a 3-(4-cyanophenyl)uracil of the formula I where $R^4$ is hydrogen in the presence of a base:

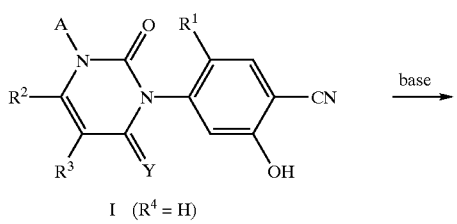

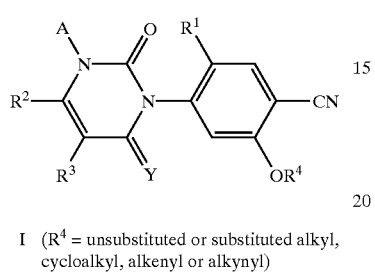

I ($R^4$ = unsubstituted or substituted alkyl, cycloalkyl, alkenyl or alkynyl)

The alkylation can be carried out, for example, using the halide, preferably the chloride or bromide, the sulfate, sulfonate, preferably the methanesulfonate (mesylate), benzenesulfonate, p-toluenesulfonate (tosylate), p-bromobenzenesulfonate (brosylate), the trifluoromethanesulfonate (triflate) or the diazo compound of an unsubstituted or substituted alkane, cycloalkane, haloalkane, alkene or alkyne.

The reaction is usually carried out in an inert organic solvent, suitable solvents being, in particular, aprotic solvents, eg. aliphatic and cyclic ethers, such as 1,2-dimethoxyethane, tetrahydrofuran and dioxane, aliphatic ketones, such as acetone, amides, such as dimethylformamide, sulfoxides, such as dimethyl sulfoxide, ureas, such as tetramethylurea and 1,3-dimethyltetrahydro-2(1H)-pyrimidinone, carboxylic esters, such as ethyl acetate, or halogenated aliphatic or aromatic hydrocarbons, such as dichloromethane and chlorobenzene.

Suitable bases are inorganic bases, eg. alkali metal carbonates, such as sodium carbonate and potassium carbonate, alkali metal hydrogencarbonates, such as sodium hydrogen carbonate and potassium hydrogen carbonate, or alkali metal hydrides, such as sodium hydride and potassium hydride, but also organic bases, eg. amines, such as triethylamine, pyridine and N,N-diethylaniline, or alkali metal alcoholates, such as sodium methanolate, sodium ethanolate and potassium tert-butanolate.

The amount of base and alkylating agent is preferably 0.5 times to twice the molar amount based on the amount of I where $R^4$=hydrogen.

In general, a reaction temperature of from 0° C. to the boiling point of the reaction mixture, in particular from 0 to 60° C., is recommended.

Any problems with regioselectivity in the case of starting compounds where A=hydrogen can be avoided in a manner known per se (use of 2 equivalents of base, introduction of a protective group etc.).

Process G):

Acylation of a 3-(4-cyanophenyl)uracil of the formula I where $R^4$ is hydrogen with a suitable alkylating agent.

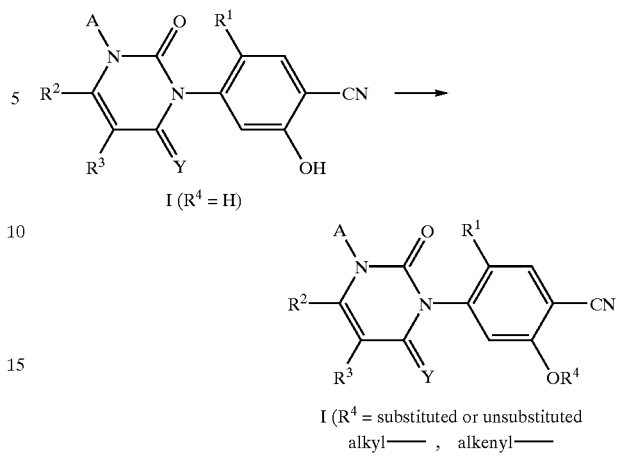

I ($R^4$ = substituted or unsubstituted alkyl——, alkenyl—— or alkynylcarbonyl)

Suitable acylating agents are for example the acid halides, in particular the acid chlorides, the anhydrides, isocyanates or sulfonylchlorides of alkane-, cycloalkane-, alkene-, alkyne-, phenyl- or phenylalkanecarboxylic acids. However, the free acids or their anhydrides are also suitable, under the condition that the process is carried out in the presence of a condensing agent, such as carbonyl diimidazole and dicyclohexylcarbodiimide.

The process is generally carried out in an inert organic solvent or diluent which is preferably aprotic, eg. in an aliphatic or cyclic ether, such as 1,2-dimethoxyethane, tetrahydrofuran and dioxane, an aliphatic ketone, such as acetone, an amide, such as dimethylformamide, a urea, such as tetramethylurea and 1,3-dimethyltetrahydro-2(1H)-pyrimidinone, a carboxylic ester, such as ethyl acetate, or an aliphatic or aromatic halogenated hydrocarbon, such as dichloromethane and chlorobenzene.

As regards suitable bases, the weight ratios and the reaction temperature, the information given for process F) applies.

Process H):

Substitution of halide by cyanide:

Process H):

Substitution of halide by cyanide:

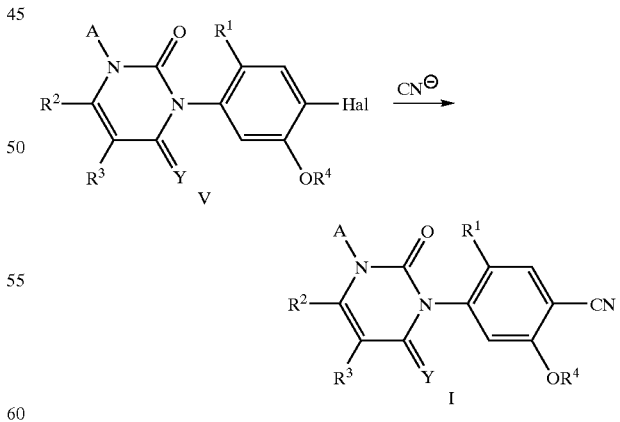

Hal is halogen, preferably fluorine, bromine or iodine.

Suitable cyanides are, in particular, metal cyanides, eg. the alkali metal cyanides, such as lithium cyanide, sodium cyanide and potassium cyanide, the alkaline earth metal cyanides, such as magnesum cyanide, or else transition metal cyanides, such as copper cyanide.

The process is usually carried out in an ether, such as tetrahydrofuran, dioxane and 1,2-dimethoxyethane, or in an aprotic polar solvent, eg. an alkyl nitrile, such as acetonitrile, propionitrile and butyronitrile, an alkylurea, such as N,N,N',N'-tetramethylurea, an open-chain or cyclic dialkylamide, such as dimethylformamide, N-methyl-2-pyrrolidone, 1,2-dimethylimidazolidin-2-one and 1,2-dimethyl-3,4,5,6-tetrahydro-2(1H)-pyrimidinone, a dialkyl sulfoxide, such as dimethyl sulfoxide, or in hexamethylphosphoric triamide.

Findings to date have revealed that the presence of a catalyst may have an advantageous effect on the course of the reaction. Examples of suitable catalysts are transition metals and their complexes or salts, eg. copper compounds, such as copper(I) chloride, copper(I) iodide, copper(I) cyanide, or nickel compounds, such as nickel bis-triphenylphosphine dibromide.

In the case of starting compounds V where A=hydrogen, it is recommended to carry out the process in the presence of a base, suitable bases being, in particular, weakly nucleophilic bases, ie. inorganic bases, eg. alkali metal carbonates, such as sodium carbonate and potassium carbonate, alkali metal hydrogen carbonates, such as sodium hydrogen carbonate and potassium hydrogen carbonate, or alkali metal hydrides, such as sodium hydride and potassium hydride, and also organic bases, eg. amines, such as triethylamine, pyridine and N,N-diethylaniline.

The weight ratios are usually not critical. In general, approximately one to 10 times the amount of cyanide and base, based on the amount of V, will suffice.

The reaction temperature is usually 50 to 250° C.; however, to increase the selectivity of the reaction, it may also be advantageous to carry out the process at lower temperatures, in particular at approximately 20° C.

With regard to various embodiments of this reaction, reference may be made to Houben-Weyl, "Methoden der Organischen Chemie" [Methods in Organic Chemistry], Georg Thieme Verlag, 4th Edition, Stuttgart 1985, Vol. E5, p. 1444 et seq., and the literature cited therein.

Process I):

Halogenation of a 3-(4-cyanophenyl)uracil of the formula I where $R^3$ is hydrogen

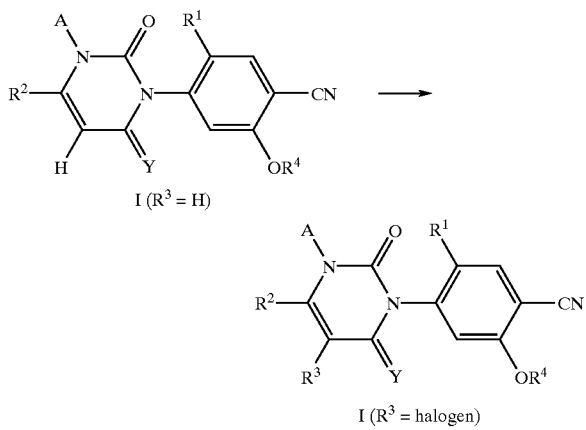

The halogenation is generally carried out in an inert organic solvent or diluent. Suitable substances for the chlorination and bromination are, for example, aliphatic carboxylic acids, such as acetic acid, or chlorinated aliphatic hydrocarbons, such as methylene chloride, chloroform and carbon tetrachloride. Low-boiling aliphatic carboxylic acids, such as acetic acid, are particularly preferred for the iodination.

Particularly suitable for the chlorination and bromination are elemental chlorine or bromine, or sulfuryl chloride and sulfuryl bromide, respectively, at from preferably 0 to 60° C., in particular 10 to 30° C.

If desired, the chlorination and bromination can be carried out in the presence of an acid binder, in which case sodium acetate and tertiary amines, such as triethylamine, dimethylaniline and pyridine, are particularly preferred.

A particularly preferred iodinating agent is elemental iodine, the reaction temperature in this case being from approximately 0 to 110° C., preferably from 10 to 30° C.

Particularly advantageous is the iodination in the presence of a mineral acid, such as fuming nitric acid.

The amount of halogenating agent is not critical; equimolar amounts of halogenating agent or an excess of up to 200 mol % based on the precursor to be halogenated are generally used.

Excess iodine can be removed for example after the reaction by means of saturated aqueous sodium hydrogen sulfite solution.

Process K):

Substitution of the nitro group of 3-(4-cyano-3-nitrophenyl)uracils VI by a group —$OR^4$:

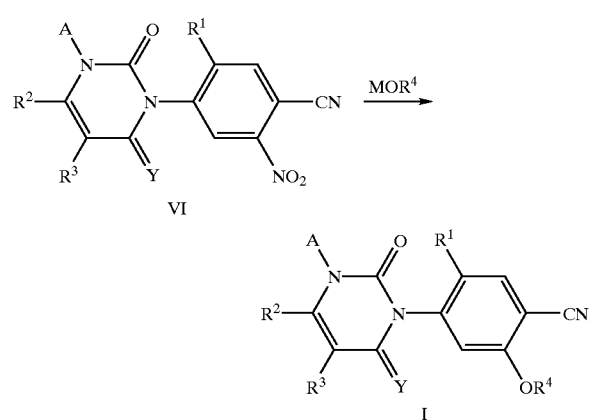

The substitution of the nitro group is generally carried out by reacting VI with an alcoholate $MOR^4$ where M is a metal atom, preferably lithium, sodium or potassium (cf., for example, Org.Synth. Coll. Vol. III, 293).

As a rule, the process is either carried out in the alcohol $HOR^4$ whose alcoholate is used, or in an inert organic solvent or diluent, eg. in an aromatic hydrocarbon, such as toluene and the xylenes, in an ether, such as diethyl ether, tetrahydrofuran and 1,2-dimethoxyethane, or in a halogenated hydrocarbon, such as dichloromethane and chlorobenzene.

The reaction temperature is generally at from 0 to 150° C., preferably from room temperature (approximately 20° C.) to the boiling point of the reaction mixture in question.

The amount of alcoholate is generally not critical; approximately 1 to 3 equivalents of alcoholate per mole of VI are preferred.

The 3-(4-cyano-3-nitrophenyl)uracils V, in turn, can be obtained for example from 3-(4-halo-3-nitrophenyl)uracils VII

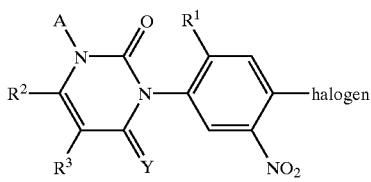

by substituting the halogen by cyano. The information given for process H) apply analogously.

The 3-(4-halo-3-nitrophenyl)uracils VII, in turn, can be prepared for example by nitrating 3-(4-halophenyl)uracils VIII

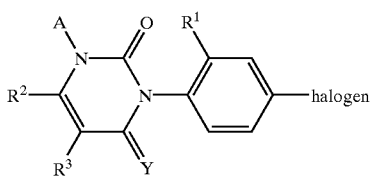

using nitric acid, nitrating acid, an inorganic nitrate, such as sodium nitrate, potassium nitrate and ammonium nitrate, or an organic nitrate, such as amyl nitrate.

Suitable solvents for the nitration are, preferably, inorganic acids, such as nitric acid and sulfuric acid, organic acids, such as acetic acid, or anhydrides, such as acetic anhydride.

The reaction temperature is usually at from (−20) to 50° C., preferably from (−10) to 30° C.

The amount of nitrating agent is not critical; it is usually one to 10 times the molar amount based on the amount of VI.

Process L):

Conversion of 3-(4-aminophenyl)uracils IX into compounds I by the Sandmeyer method:

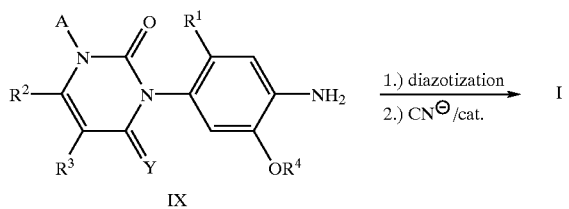

In this type of reaction, a procedure is generally followed in which the amino group is converted into the diazonium salt in a manner known per se, and this diazonium salt is subsequently reacted with a metal cyanide, preferably lithium cyanide, sodium cyanide or potassium cyanide, in the presence of a transition metal catalyst, in particular copper(I) salt, expediently copper(I) cyanide.

As regards the process conditions, reference may be made, for example, to the information given in C. Ferri, "Reaktionen der organischen Chemie" [Reactions in Organic Chemistry], Georg Thieme Verlag, Stuttgart 1978, p. 319, and in Organic Synthesis Coll. Vol 1, p. 514 (1941).

The starting compounds IX can preferably be prepared by reducing the corresponding nitro compounds using hydrogen in the presence of a metal catalyst composed of Raney nickel, palladium or platinum, or using a reducing agent, eg. a tin(II) salt or iron. Further information on this reaction, which is known per se, can be found, for example, in DE-A 37 24 399.

The nitrated precursors corresponding to the compounds IX, in turn, can expediently be obtained by nitrating phenyl compounds X

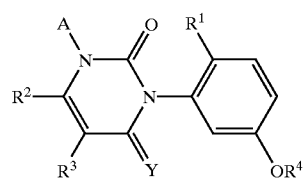

The information given for the nitration of the 3-(4-halophenyl)uracils VII in process K) applies analogously to the nitration of the phenyluracils X.

Process M):

Direct cyanation of a phenyl compound X:

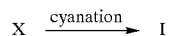

The cyanation can be carried out in the absence of a solvent or in an inert solvent or diluent, for example in an aliphatic, cyclic or aromatic hydrocarbon, such as n-pentane, petroleum ether and cyclohexane, an aliphatic or cyclic ether, such as diethyl ether, tert-butyl methyl ether, dimethoxyethane and tetrahydrofuran, an aliphatic or aromatic halohydrocarbon, such as dichloromethane, chloroform, 1,2-dichloroethane and the dichlorobenzenes, an alcohol, such as ethanol, methanol and tert-butanol, an amide, such as dimethylformamide and n-methylpyrrolidone, or an amine, such as ammonia. Mixtures of these are also suitable.

Suitable cyanide sources are alkyl thiocyanates, such as methyl thiocyanate {cf., for example, Synth. Commun. 20, 71 (1990)}, chlorosulfonyl isocyanate (cf., for example, Org. Synth. Coll. Vol VI, p. 465), dicyan, chlorine cyanide and bromine cyanide, and furthermore trichloroacetonitrile {cf., in this context, Gazz. Chim. Ital. 122, 283 (1992)}.

The temperatures are usually at from (−20) to 150° C., preferably at from (−10)° C. to the boiling point of the reaction mixture in question.

The ratio of cyanating agent to IX is not critical; it is usually at from 1:1 to 10:1.

Modifications of this reaction are described, inter alia, in Houben-Weyl, "Methoden der Organischen Chemie" [Methods in Organic Chemistry], Georg Thieme Verlag, Vol. E5, 4th Edition, Stuttgart 1985, p. 1447 et seq. and in the literature cited therein.

Those starting compounds of the formulae VI, VII, VIII and IX which are not known already can be prepared in a manner known per se (cf., for example, EP-A 255 047, EP-A 517 181 and JP-A 05/025 143).

The enamine esters of the formula III are novel. They can also be employed as herbicides.

They can be prepared by methods known per se, for example by one of the following processes:

N):

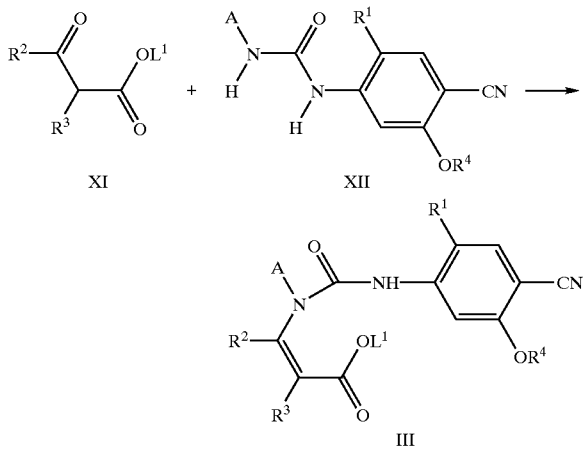

The process is preferably carried out under essentially anhydrous conditions in an inert solvent or diluent, particularly preferably in the presence of an acidic or basic catalyst.

Suitable solvents or diluents are, in particular, organic solvents which can be mixed with water to give an azeotropic mixture, for example aromatics, such as benzene, toluene and o-, m- and p-xylene, halogenated hydrocarbons, such as methylene chloride, chloroform, carbon tetrachloride and chlorobenzene, aliphatic and cyclic ethers, such as 1,2-dimethoxyethane, tetrahydrofuran and dioxane, or cyclohexane, but also alcohols, such as methanol and ethanol.

Preferred suitable acidic catalysts are strong mineral acids, such as sulfuric acid and hydrochloric acid, phosphorus-containing acids, such as orthophosphoric acid and polyphosphoric acid, organic acids, such as p-toluenesulfonic acid, and acidic cation exchangers, such as "Amberlyst 15" (Fluka).

Examples of suitable basic catalysts are metal hydrides, such as sodium hydride, and, particularly preferably, metal alcoholates, such as sodium methanolate and sodium ethanolate.

XI and the β-ketoester XII are expediently employed in an approximately stoichiometric ratio, or else the process is carried out with a slight excess of one or the other component, up to approximately 10 mol %.

An amount of catalyst of 0.5 to 2 mol % based on the amount of precursor will usually suffice.

In general, the reaction is carried out at from 60 to 120° C. or, to rapidly remove water which forms, preferably up to the boiling point of the reaction mixture.

O):

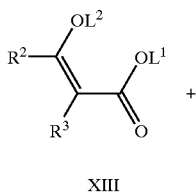

-continued

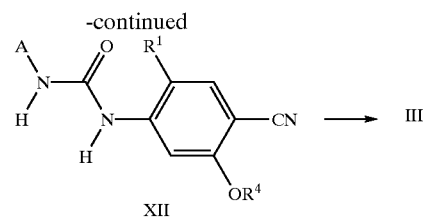

$L^2$ is $C_1$–$C_4$-alkyl or phenyl.

This reaction can be carried out, for example, in an inert organic solvent which is miscible with water, for example an aliphatic or cyclic ether, such as 1,2-dimethoxyethane, tetrahydrofuran and dioxane, or a lower alcohol, in particular ethanol, the reaction temperature usually being at from 50 to 100° C., preferably at the boiling point of the reaction mixture.

However, the reaction can also be carried out in an aromatic diluent, such as benzene, toluene and o-, m- or p-xylene, in which case an addition of either an acidic catalyst, such as hydrochloric acid and p-toluenesulfonic acid, or of a base, eg. an alkali metal alcoholate, such as sodium methanolate and sodium ethanolate, is recommended. In this process variant, the reaction temperature is usually again at from 50 to 100° C., but preferably at from 60 to 80° C.

With regard to the weight ratios, the information given for method N) applies.

P):

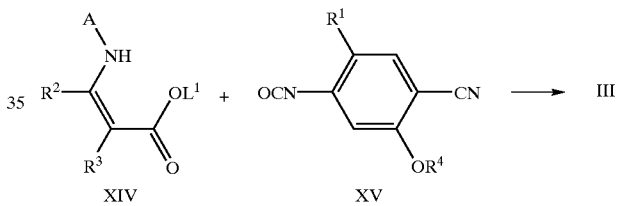

The reaction is expediently carried out in the presence of an essentially anhydrous aprotic organic solvent or diluent, for example an aliphatic or cyclic ether, such as diethyl ether, 1,2-dimethoxyethane, tetrahydrofuran and dioxane, an aliphatic or aromatic hydrocarbon, such as n-hexane, benzene, toluene and o-, m- or p-xylene, a halogenated, aliphatic hydrocarbon, such as methylene chloride, chloroform, carbon tetrachloride, 1,2-dichloroethane and chlorobenzene, an aprotic, polar solvent, such as dimethylformamide, hexamethylphosphoric triamide and dimethyl sulfoxide, or a mixtures of these.

If desired, the process can also be carried out in the presence of a metal hydride base, such as sodium hydride and potassium hydride, or an organic tertiary base, such as triethylamine and pyridine, it being possible for the organic base to act simultaneously as the solvent.

It is expedient to employ the precursors in a stoichiometric ratio or with a slight excess of one or the other components of up to approximately 10 mol %. If the process is carried out in the absence of a solvent and in the presence of an organic base, the latter will be present in a larger excess.

The reaction temperature is preferably at from (−80) to 50° C., in particular at from (−60) to 30° C.

In a particularly preferred embodiment, the enamine ester III obtained is converted directly (ie. "in situ") into the corresponding desired product I in accordance with process A), using an excess of base.

Q):

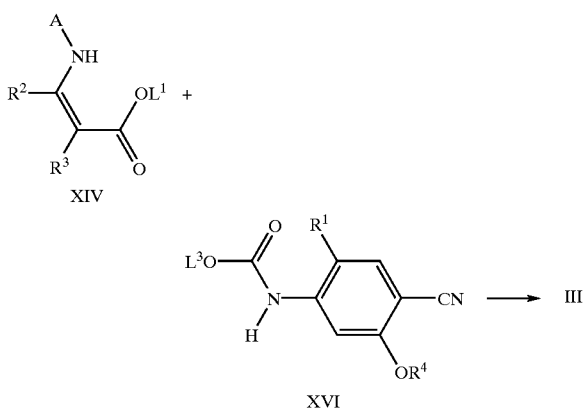

$L^3$ is $C_1$–$C_4$-alkyl or phenyl.

This reaction is expediently carried out in an aprotic, polar solvent or diluent, such as dimethylformamide, 2-butanone, dimethyl sulfoxide and acetonitrile, advantageously in the presence of a base, for example an alkali metal alcoholate or alkaline earth metal alcoholate, in particular a sodium alkanolate, such as sodium methanolate, an alkali metal carbonate or alkaline earth metal carbonate, in particular sodium carbonate, or an alkali metal hydride, such as lithium hydride and sodium hydride.

Once to twice the molar amount of base, based on the amount of XIV or XVI, will usually suffice.

The reaction temperature is generally at from 80 to 180° C., preferably at the boiling point of the reaction mixture.

As regards the weight ratios of the starting compounds, the information given for method N) applies.

In a particularly preferred embodiment, a sodium alcoholate is used as the base, and the alcohol which forms in the course of the reaction is continuously distilled off. The enamine esters III prepared in this manner can be cyclized without isolation from the reaction mixture in accordance with process A) to give a salt of the substituted 3-(4-cyanophenyl)uracils I.

R):

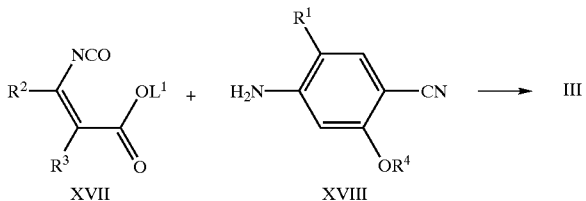

This reaction is expediently carried out in the presence of an essentially anhydrous aprotic organic solvent or diluent, for example an aliphatic or cyclic ether, such as diethyl ether, 1,2-dimethoxyethane, tetrahydrofuran and dioxane, an aliphatic or aromatic hydrocarbon, such as n-hexane, benzene, toluene and o-, m- or p-xylene, a halogenated, aliphatic hydrocarbon, such as methylene chloride, chloroform, carbon tetrachloride, 1,2-dichloroethane and chlorobenzene, an aprotic, polar solvent, such as dimethylformamide, hexamethylphosphoric triamide and dimethyl sulfoxide, or a mixtures of these.

If desired, the process can also be carried out in the presence of a metal hydride base, such as sodium hydride and potassium hydride, an alkali metal alcoholate or alkaline earth metal alcoholate, such as sodium methanolate, sodium ethanolate and potassium tert-butanolate, or an organic nitrogen base, such as triethylamine and pyridine, it being possible for the organic base to act simultaneously as the solvent.

It is expedient to employ the precursors in a stoichiometric ratio or with an excess of one of the components of up to approximately 20 mol %. If the process is carried out in the absence of a solvent and in the presence of an organic base, the latter is advantageously present in an even larger excess.

The reaction temperature is generally at from (−80) to 150° C., preferably at from (−30)° C. to the boiling point of the reaction mixture in question.

The enamine carboxylates of the formula IV are also novel; they too can be prepared in a manner known per se, for example from an aniline derivative of the formula VIII by the following equation:

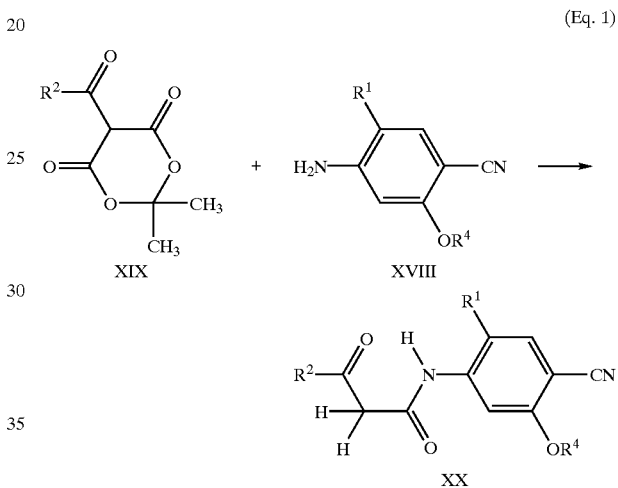

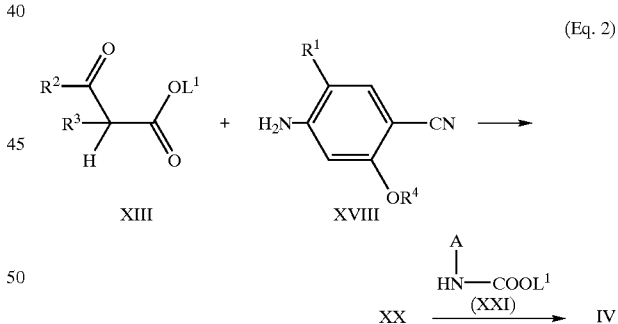

The reaction in accordance with equation 1 is preferably carried out in an anhydrous inert aprotic solvent, for example in a halogenated hydrocarbon, such as methylene chloride, chloroform, carbon tetrachloride and chlorobenzene, an aromatic hydrocarbon, such as benzene, toluene and o-, m- or p-xylene, or an aliphatic or cyclic ether, such as diethyl ether, dibutyl ether, 1,2-dimethoxyethane, tetrahydrofuran and dioxane.

For the reaction of XIX with XVIII in accordance with equation (Eq. 1), the reaction temperature is generally at from approximately 70 to 140° C., in particular from 100 to 120° C.

The reaction in accordance with equation (Eq. 2) is an aminolysis, which is generally carried out either in the absence of a solvent [cf., for example, J. Soc. Dyes Col. 42, (1926), 81, Ber. 64, (1931), 970; Org. Synth., Coll. Vol. IV, (1943), 80 and J.A.C.S. 70, (1948), 2402] or in an inert anhydrous solvent/diluent, in particular an aprotic solvent, for example in an aromatic, such as toluene and o-, m- or p-xylene, or a halogenated aromatic, such as chlorobenzene.

It is recommended to carry out the process in the presence of a basic catalyst, for example a higher-boiling amine [see, for example, Helv. Chim. Acta 11, (1928), 779 and U.S. Pat. No. 2,416,738] or pyridine.

The reaction temperature is preferably at from approximately 130 to 160° C.

In both reactions {(Eq. 1) and (Eq. 2)}, the starting compounds are expediently employed in approximately stoichiometric amounts, or else the process is carried out with a slight excess of one or the other component of up to approximately 10 mol %. If the process is carried out in the presence of a basic catalyst, an amount of 0.5 to 2 mol % of catalyst based on the amount of one of the educts will usually suffice.

The subsequent reaction of the resulting compounds of the formula XX with the amine XXI is advantageously carried out in an essentially anhydrous solvent/diluent under atmospheric pressure, particularly preferably in the presence of an acidic catalyst.

It is advisable to prepare enamine carboxylates IV where A is amino by employing compounds XXI having a protected amino group (for example in the form of a hydrazone).

Suitable solvents/diluents are, in particular, organic liquids which can be mixed with water to given an azeotropic mixture, for example aromatics, such as benzene, toluene and o-, m- or p-xylene, or halogenated hydrocarbons, such as carbon. tetrachloride and chlorobenzene.

Suitable catalysts are, in particular, strong mineral acids, such as sulfuric acid, organic acids, such as p-toluenesulfonic acid, phosphorus-containing acids, such as orthophosphoric acid and polyphosphoric acid, or acidic cation exchangers, such as "Amberlyst 15" (Fluka).

The reaction temperature is generally at from approximately 70 to 150° C.; however, to rapidly remove the water of reaction which forms it is expedient to carry out the process at the boiling point of the reaction mixture in question.

Unless otherwise specified, all processes described above are expediently carried out under atmospheric pressure or under the inherent pressure of the reaction mixture in question.

Working-up of the reaction mixtures is generally carried out by methods known per se, for example by removing the solvent, partitioning the residue in a mixture of water and a suitable organic solvent and working up the organic phase to obtain the product.

The 3-(4-cyanophenyl)uracils of the formula I can have one or more chiral centers, in which case they are usually obtained as enantiomer or diastereomer mixtures. If desired, the mixtures can be separated into the essentially pure isomers by customary methods, for example by means of crystallization or chromatography on an optically active adsorbate. Pure optically active isomers can, for example, also be prepared from the corresponding optically active starting materials.

3-(4-Cyanophenyl)uracils I where A is hydrogen can be converted into their salts, preferably their alkali metal salts, in a manner known per se (cf., in this context, also preparation method b)).

Salts of I whose metal ion is other than an alkali metal ion can be prepared in the customary manner by double decomposition of the corresponding alkali metal salt, and ammonium, phosphonium, sulfonium and sulfoxonium salts by means of ammonia, phosphonium hydroxides, sulfonium hydroxides or sulfoxonium hydroxides.

The compounds I and their agriculturally useful salts, in the form of the isomer mixtures and of the pure isomers, are suitable as herbicides. The herbicidal compositions comprising I provide very effective control of vegetation on non-crop areas, particularly at high application rates. They act against broad-leaved weeds and grass weeds in crops such as wheat, rice, maize, soybeans and cotton without damaging the crop plants considerably. This effect is particularly pronounced at low application rates.

Depending on the application method in question, the compounds I or the herbicidal compositions comprising them can additionally be used in a further number of crop plants for eliminating undesirable plants. Suitable crops are, for example, the following:

Allium cepa, Ananas comosus, Arachis hypoqaea, Asparagus officinalis, Beta vulgaris ssp. altissima, Beta vulgaris ssp. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum (N.rustica), Olea europaea, Oryza sativa , Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera and Zea mays.

In addition, the compounds I can also be used in crops which tolerate the action of herbicides as a result of breeding, including genetic engineering methods.

Moreover, the 3-(4-cyanophenyl)uracils I are also suitable for the desiccation and/or defoliation of plants.

As desiccants, they are particularly suitable for desiccating the aerial parts of crop plants such as potatoes, oilseed rape, sunflowers and soybeans. This allows completely mechanical harvesting of these important crop plants.

Also of economic interest is facilitating harvesting, which is made possible by concentrating, over a period of time, the drop or the reduction of adhesion to the tree of citrus fruit, olives or other species and varieties of pomaceous fruit, stone fruit and shell fruit. The same mechanism, ie. promotion of the formation of abscission tissue between fruit or leaf and shoot of the plants, is also essential for the targeted controllable defoliation of economic plants, in particular cotton.

Moreover, shortening the period of time within which the individual cotton plants mature results in an increased fiber quality post-harvest.

The compounds I, or the compositions comprising them, can be applied, for example, in the form of ready-to-spray aqueous solutions, powders, suspensions, also highly concentrated aqueous oily or other suspensions or dispersions, emulsions, oil dispersions, pastes, dusts, materials for spreading, or granules, by means of spraying, atomizing, dusting, scattering or pouring. The use forms depend on the intended purposes; in any case, they should guarantee the finest possible distribution of the active ingredients according to the invention.

Suitable inert additives for the preparation of ready-to-spray solutions, emulsions, pastes or oil dispersions are essentially: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols, such as methanol, ethanol, propanol, butanol and cyclohexanol, ketones, such as cyclohexanone, strongly polar solvents, eg. amines, such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substrates, either as such or dissolved in an oil or solvent, can be homogenized in water by means of a wetting agent, tackifier, dispersant or emulsifier. Alternatively, it is possible to prepare concentrates comprising active ingredient, wetting agent, tackifier, dispersant or emulsifier and, if desired, solvent or oil, and these concentrates are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, or of fatty acids, alkyl- and alkylaryl sulfonates, alkyl, lauryl ether and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, urea, and products of vegetable origin, such as cereal meal, tree bark meal, wood meal and nutshell meal, cellulose powder, or other solid carriers.

The concentrations of the active ingredients I in the ready-to-use products can be varied within wide ranges. In general, the formulations comprise from 0.001 to 98% by weight, preferably from 0.01 to 95% by weight, of active ingredient. The active ingredients are employed in a purity of from 90% to 100%, preferably 95% to 100% (in accordance with NMR spectrum).

The formulation examples which follow illustrate the preparation of such products:

I. 20 parts by weight of Compound No. I.01 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

II. 20 parts by weight of Compound No. I.02 are dissolved in a mixture composed of 40 parts by weight of cyclohexanone, 30 parts by weight of isobutanol, 20 parts by weight of the adduct of 7 mol of ethylene oxide to 1 mol of isooctyl phenol and 10 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

III. 20 parts by weight of the active ingredient No. I.03 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

IV. 20 parts by weight of the active ingredient No. I.04 are mixed thoroughly with 3 parts by weight of sodium diisobutylnaphthalene-α-sulfonic acid, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture comprising 0.1% by weight of the active ingredient.

V. 3 parts by weight of the active ingredient No. I.05 are mixed with 97 parts by weight of finely divided kaolin. This gives a dust comprising 3% by weight of the active ingredient.

VI. 20 parts by weight of the active ingredient No. I.06 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of Compound No. I.07 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of Compound No. I.08 is dissolved in a mixture composed of 80 parts by weight of cyclohexanone and 20 parts by weight of Emulphor EL[1]). This gives a stable emulsion concentrate.

1) ethoxylated castor oil

The active ingredients I, or the herbicidal compositions, can be applied pre- or post-emergence. If the active ingredients are less well tolerated by certain crop plants, application techniques may be used where the herbicidal compositions are sprayed, with the aid of the spraying equipment, in such a way that the active ingredients come into as little contact as possible with the leaves of the sensitive crop plants while reaching the leaves of undesirable plants which grow thereunder, or the naked soil surface (post-directed, lay-by).

The application rates of active-ingredient I are from 0.001 to 3.0, preferably 0.01 to 1, kg of active ingredient (a.i.) per ha, depending on the desired control, the season, the target plants and the growth stage.

To widen the spectrum of action and to achieve synergistic effects, the 3-(4-cyanophenyl)uracils I may be mixed with a large number of representatives of other groups of herbicidal or growth-regulating active ingredients and then applied concomitantly. Suitable components for mixtures are, for example, 1,2,4-thiadiazoles, 1,3,4-thiadiazoles, amides, aminophosphoric acid and derivatives thereof, aminotriazoles, anilides, aryloxy-/hetaryloxyalkanoic acids and derivatives thereof, benzoic acid and derivatives thereof, benzothiadiazinones, 2-(hetaroyl/aroyl)-1,3-cyclohexanediones, heteroaryl aryl ketones, benzylisoxazolidinones, meta-CF₃-phenyl derivatives, carbamates, quinolinecarboxylic acid and derivatives thereof, chloroacetanilides, cyclohexane-1,3-dione derivatives, diazines, dichloropropionic acid and derivatives thereof, dihydrobenzofurans, dihydrofuran-3-one, dinitroanilines, dinitrophenols, diphenyl ethers, dipyridylium compounds, halocarboxylic acids and derivatives thereof, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic esters, phenylacetic acid and derivatives thereof, 2-phenylpropionic acid and derivatives thereof, pyrazoles, phenylpyrazoles, pyridazines, pyridinecarboxylic acid and derivatives thereof, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, together with further crop protection agents, for example with pesticides or agents for controlling pests, phytopathogenic fungi or bacteria. Also of interest is the miscibility with mineral salt solutions, which are employed for treating nutrient and trace element deficiencies. Nonphytotoxic oils and oil concentrates may also be added.

PREPARATION EXAMPLES

Example 1

3-[4-Cyano-3-methoxyphenyl]-6-trifluoromethyl-1,2,3,4-tetrahydro-pyrimidine-2,4-dione (Comp. 1.01)

Sodium methanolate solution (2.8 g of a 30 percent strength solution in methanol) was added to a solution of 3-[4-cyano-3-nitrophenyl]-6-trifluoromethyl-1,2,3,4-tetrahydro-pyrimidine-2,4-dione (2.4 g) in 50 ml of anhydrous methanol. The reaction mixture was subsequently refluxed for 5 hours. After cooling, water (50 ml) was added first, followed by 10% strength aqueous hydrochloric acid to a pH of 3–4. The precipitate formed was subsequently separated off, washed with water and petroleum ether and dried. Yield: 1.1 g; m.p.: >230° C.

Example 2

1-Amino-3-[4-cyano-3-methoxyphenyl]-6-trifluoromethyl-1,2,3,4-tetrahydropyrimidine-2,4-dione (Comp. 1.02)

Potassium carbonate (1.0 g) and 2,4-dinitrophenoxyamine (0.8 g) were added to a solution of 3-[4-cyano-3-methoxyphenyl]-6-trifluoromethyl-1,2,3,4-tetrahydropyrimidine-2,4-dione (1.1 g) in 15 ml of ethyl acetate. The mixture was subsequently stirred for 15 hours at 55–60° C., whereupon the solids formed were separated off and washed using in each case 30 ml of ethyl acetate and diisopropyl ether. The combined filtrates were washed twice using in each case 25 ml of water, dried over sodium sulfate and then concentrated. After crystallization using 10 ml of diisopropyl ether, 0.6 g of the desired product was obtained. M.p.: >230° C.

Example 3

1-Amino-3-[4-cyano-3-hydroxyphenyl]-6-trifluoromethyl-1,2,3,4-tetrahydropyrimidine-2,4-dione (Comp. 1.07)

1-Amino-3-[4-cyano-3-methoxyphenyl]-6-trifluoromethyl-1,2,3,4-tetrahydropyrimidine-2,4-dione (2.0 g) and pyridinium hydrochloride (2.1 g) were stirred for 2 hours at 200–210° C. After cooling, the reaction mixture was dissolved in 100 ml of n-butanol, whereupon the solution was washed three times using in each case 30 ml of water. The organic phase was dried over sodium sulfate and subsequently freed from solvent. After crystallization using 10 ml of diisopropyl ether and chromatographic purification of the crude product (eluent: dichloromethane/ethyl acetate= 9:1 to 1:1), 0.4 g of the desired product was obtained. M.p.: >230° C.

Example 4

3-[3-Allyloxy-4-cyanophenyl]-1-methyl-6-trifluoromethyl-1,2,3,4-tetrahydropyrimidine-2,4-dione (Comp. 1.08)

Potassium carbonate (4.6 g) and methyl iodide (2.1 ml, dissolved in 20 ml of dimethylformamide) were added to a solution of 3-[3-allyloxy-4-cyanophenyl]-1-methyl-6-trifluoromethyl-1,2,3,4-tetrahydropyrimidine-2,4-dione (10.1 g) in 130 ml of dimethylformamide. After the reaction mixture had been stirred for 20 hours at room temperature, 150 ml of water were added, whereupon the precipitate formed was separated off, washed with water and petroleum ether and dried. Yield: 2.5 g; m.p.: 158–160° C.

In addition to those mentioned above, other 3-(4-cyanophenyl)uracils I which were prepared, or can be prepared, in a similar manner are listed in Table 2 below:

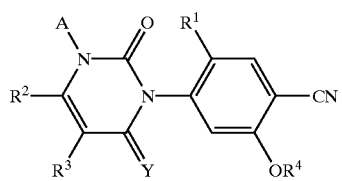

I

| No. | Y | A | R¹ | R² | R³ | R⁴ | M.p. [° C.] |
|---|---|---|---|---|---|---|---|
| 1.01 | O | H | H | CF₃ | H | CH₃ | >230 |
| 1.02 | O | NH₂ | H | CF₃ | H | CH₃ | >230 |
| 1.03 | O | H | H | CF₃ | H | CH₂CH=CH₂ | 208–210 |
| 1.04 | O | NH₂ | H | CF₃ | H | CH₂CH=CH₂ | 177–179 |
| 1.05 | O | CH₃ | H | CF₃ | H | CH₃ | >230 |
| 1.06 | O | H | H | CF₃ | H | CH(CH₃)₂ | 180–184 |
| 1.07 | O | NH₂ | H | CF₃ | H | H | >230 |
| 1.08 | O | CH₃ | H | CF₃ | H | CH₂CH=CH₂ | 158–1600 |

-continued

Structure I:

| No. | Y | A | R¹ | R² | R³ | R⁴ | M.p. [° C.] |
|-----|---|------|-----|-----|----|----------|---------|
| 1.09 | O | NH₂ | H | CF₃ | H | CH(CH₃)₂ | 185–187 |
| 1.10 | O | H | H | CF₃ | H | C₂H₅ | >230 |

Preparation of the starting compounds:

Example 5

3-[4-Cyano-3-nitrophenyl]-6-trifluoromethyl-1,2,3,4-tetrahydropyrimidine-2,4-dione Potassium carbonate (16.6 g) and potassium cyanide (7.8 g) were added to a solution of 3-[4-fluoro-3-nitrophenyl]-6-trifluoromethyl-1,2,3,4-tetrahydropyrimidine-2,4-dione (31.9 g) in 250 ml of anhydrous N,N-dimethylformamide. The reaction mixture was subsequently stirred for a total of 45 hours at 75–80° C., with two further additions of potassium cyanide (in total 4.6 g) since the reaction had not proceeded completely. For working-up, water (250 ml) was added to the reaction mixture after it had cooled. The pH was subsequently brought to 2–3 by adding 60 ml of 1 N. hydrochloric acid. After nitrogen had been passed through the mixture for 4 hours to expel the hydrocyanic acid which had been liberated, the precipitate formed was separated off, washed with water and petroleum ether and dried. Yield: 17.0 g; m.p.: 135° C.

Example 6

3-[4-Cyano-2-fluoro-5-nitrophenyl]-1-methyl-6-trifluoromethyl-1,2,3,4-tetrahydropyrimidine-2,4-dione (Comp. 8.2)

Potassium cyanide (0.5 g) was added to a solution of 3-[2,4-difluoro-5-nitrophenyl]-1-methyl-6-trifluoromethyl-1,2,3,4-tetrahydropyrimidine-2,4-dione (2.5 g) in 50 ml of anhydrous dimethyl sulfoxide. The reaction mixture was subsequently stirred for 10 hours at room temperature, more potassium cyanide (0.16 g) being added after 5 hours. For working-up, most of the solvent was removed at 80° C. under a high vacuum. The residue was taken up in 150 ml of water, washed three times using in each case 30 ml of water, dried over sodium sulfate and concentrated. Chromatography on silica gel (dichloromethane as eluent) and crystallization using petroleum ether gave 1.2 g of the desired product; m.p.: 155–157° C. The following compounds of Table 3 were prepared in a similar manner:

Structure VIII:

| No. | Y | A | R¹ | R² | R³ | M.p. [° C.] |
|-----|---|-----|---|-----|----|---------|
| 8.1 | O | H | H | CF₃ | H | 135 |
| 8.2 | O | CH₃ | F | CF₃ | H | 155–157 |
| 8.3 | O | H | F | CF₃ | H | 135–137 |

Use Examples (Herbicidal Activity)

The herbicidal action of the 3-(4-cyanophenyl)uracils I was demonstrated by the following greenhouse experiments:

The culture containers used were plastic flower pots containing loamy sand with approximately 3.0% of humus as the substrate. The seeds of the test plants were sown separately for each species.

In the case of the pre-emergence treatment, the active ingredients, which were suspended or emulsified in water, were applied directly after sowing by means of finely distributing nozzles. The containers were irrigated gently to promote germination and growth and subsequently covered with translucent plastic hoods until the plants had rooted. This cover results in uniform germination of the test plants, unless this was adversely affected by the active ingredients.

For the post-emergence treatment, the test plants were first grown to a plant height of 3 to 15 cm, depending on the growth form, and only then treated with the active ingredients which were suspended or emulsified in water. The test plants were either sown directly and grown in the same containers, or grown separately as seedlings and transplanted to the test containers a few days prior to treatment. The application rate for the post-emergence treatment was 0.0156 or 0.0078 kg of a.i. (active ingredient) per ha.

The plants were kept at from 10–25° C. or 20–35° C., depending on the species. The test period extended to 2–4 weeks. During this time, the plants were tended and their response to individual treatments was evaluated.

Evaluation was carried out using a scale from 0 to 100. 100 means no emergence of the plants, or complete destruction of at least the aerial parts, and 0 means no damage or normal course of growth.

The plants used for the greenhouse experiments were the following species:

| Scientific Name | Common Name |
|---|---|
| *Abutilon theophrasti* | velvet leaf |
| *Galium aparine* | catchweed bedstraw |
| *Ipomoea subspecies* | morningglory |
| *Solanum nigrum* | black nightshade |

At an application rate of 0.0156 or 0.0078 kg of a.i./ha, compound No. I.02 was very effective against the above-mentioned plants when used post-emergence.

Use examples (Desiccant/Defoliant Activity)

The test plants used were young cotton plants with 4 leaves (without cotyledons) which had been grown under greenhouse conditions (relative atmospheric humidity 50 to 70%; day/night temperature=27/20° C.).

The young cotton plants underwent foliar treatment to runoff point with aqueous preparations of the active ingredients (with an addition of 0.15% by weight of the fatty alcohol alkoxylate Plurafac LF 700 based on the spray mixture). The amount of water applied was 1000 l/ha (converted). After 13 days, the number of shed leaves and the degree of defoliation in % were determined.

No leaves were shed in the untreated control plants.

We claim:

1. A compound of formula I

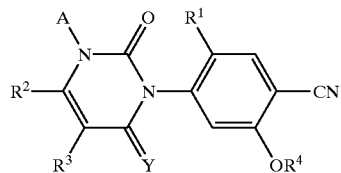

(I)

wherein

A is methyl;

Y is oxygen or sulfur;

$R^1$ is hydrogen or fluorine;

$R^2$ is trifluoromethyl;

$R^3$ is hydrogen; and $R^4$ is hydrogen, methyl, isopropyl, propargyl, $CH_2$—$COOCH_3$, $CH_2$—$COOC_2H_5$, $CH(CH_3)$—$COOCH_3$ or $CH(CH_3)$—$COOC_2H_5$.

2. The compound of formula I defined in claim 1, wherein $R^4$ denotes methyl, isopropyl, propargyl, $CH_2$—$COOCH_3$, $CH_2$—$COOC_2H_5$, $CH(CH_3)$—$COOCH_3$ or $CH(CH_3)$—$COOC_2H_5$.

3. The compound of formula I defined in claim 1 wherein Y is oxygen.

4. A herbicidal composition comprising an effective amount of at least one compound of formula I

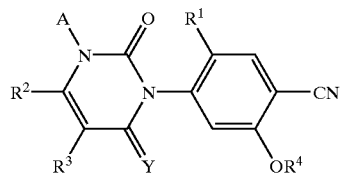

(I)

wherein

A is methyl;

Y is oxygen or sulfur;

$R^1$ is hydrogen or fluorine;

$R^2$ is trifluoromethyl;

$R^3$ is hydrogen; and $R^4$ is hydrogen, methyl, isopropyl, propargyl, $CH_2$—$COOCH_3$, $CH_2$—$COOC_2H_5$, $CH(CH_3)$—$COOCH_3$ or $CH(CH_3)$—$COOC_2H_5$, or of an agriculturally useful salt thereof, and at least one inert liquid or solid carrier and optionally at least one surfactant.

5. A composition for the desiccation or defoliation of plants, comprising an effective amount of at least one compound of formula I

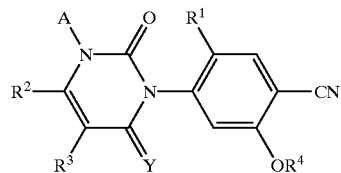

(I)

wherein

A is methyl;

Y is oxygen or sulfur;

$R^1$ is hydrogen or fluorine;

$R^2$ is trifluoromethyl;

$R^3$ is hydrogen; and $R^4$ is hydrogen, methyl, isopropyl, propargyl, $CH_2$—$COOCH_3$, $CH_2$—$COOC_2H_5$, $CH(CH_3)$—$COOCH_3$ or $CH(CH_3)$—$COOC_2H_5$, or of an agriculturally useful salt thereof, and at least one inert liquid or solid carrier and optionally at least one surfactant.

6. The composition defined in claim 4, wherein $R^4$ denotes methyl, isopropyl, propargyl, $CH_2$—$COOCH_3$, $CH_2$—$COOC_2H_5$, $CH(CH_3)$—$COOCH_3$ or $CH(CH_3)$—$COOC_2H_5$.

7. The composition defined in claim 5, wherein $R^4$ denotes methyl, isopropyl, propargyl, $CH_2$—$COOCH_3$, $CH_2$—$COOC_2H_5$, $CH(CH_3)$—$COOCH_3$ or $CH(CH_3)$—$COOC_2H_5$.

8. A method of controlling undesired vegetation, which comprises allowing an effective amount of at least one compound of formula I

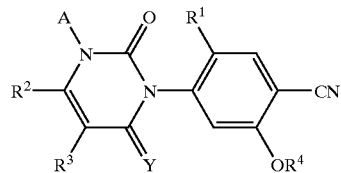

(I)

wherein

A is methyl;

Y is oxygen or sulfur;

$R^1$ is hydrogen or fluorine;

$R^2$ is trifluoromethyl;

$R^3$ is hydrogen; and $R^4$ is hydrogen, methyl, isopropyl, propargyl, $CH_2$—$COOCH_3$, $CH_2$—$COOC_2H_5$, $CH(CH_3)$—$COOCH_3$ or $CH(CH_3)$—$COOC_2H_5$, or of an agriculturally useful salt thereof, to act on plants, their habitat or on seed.

9. A method for desiccating or defoliating plants, which comprises applying to the plants an effective amount of at least one compound of formula I

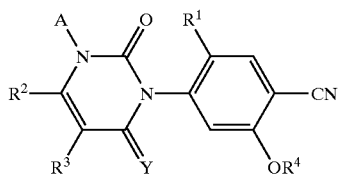

wherein

A is methyl;

Y is oxygen or sulfur;

$R^1$ is hydrogen or fluorine;

$R^2$ is trifluoromethyl;

$R^3$ is hydrogen; and $R^4$ is hydrogen, methyl, isopropyl, propargyl, $CH_2$—$COOCH_3$, $CH_2$—$COOC_2H_5$, $CH(CH_3)$—$COOCH_3$ or $CH(CH_3)$—$COOC_2H_5$, or an agriculturally useful salt thereof.

10. The method of claim 8, wherein $R^4$ denotes methyl, isopropyl, propargyl, $CH_2$—$COOCH_3$, $CH_2$—$COOC_2H_5$, $CH(CH_3)$—$COOCH_3$ or $CH(CH_3)$—$COOC_2H_5$.

11. The method of claim 9, wherein $R^4$ denotes methyl, isopropyl, propargyl, $CH_2$—$COOCH_3$, $CH_2$—$COOC_2H_5$, $CH(CH_3)$—$COOCH_3$ or $CH(CH_3)$—$COOC_2H_5$.

* * * * *